US012334212B2

(12) United States Patent
Weaver et al.

(10) Patent No.: US 12,334,212 B2
(45) Date of Patent: Jun. 17, 2025

(54) VIRTUAL AUGMENTATION OF CLINICAL CARE ENVIRONMENTS

(71) Applicant: CERNER INNOVATION, INC., Kansas City, MO (US)

(72) Inventors: Paul Weaver, Overland Park, KS (US); Jay Christopher Vaglio, Mission, KS (US); Anna-Therese Fowler, Leawood, KS (US); Alex Lende, Kansas City, MO (US); Eric A. Wilson, Lee's Summit, MO (US); Mayur Rajendran, Overland Park, KS (US); Grant Taylor Floyd, Kansas City, MO (US); Matt Ryan Anderson, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 18/382,096

(22) Filed: Oct. 20, 2023

(65) Prior Publication Data
US 2024/0047046 A1 Feb. 8, 2024

Related U.S. Application Data

(63) Continuation of application No. 17/482,990, filed on Sep. 23, 2021, now Pat. No. 11,817,205, which is a (Continued)

(51) Int. Cl.
*G16H 30/40* (2018.01)
*G06F 3/01* (2006.01)
(Continued)

(52) U.S. Cl.
CPC .............. *G16H 30/40* (2018.01); *G06F 3/013* (2013.01); *G06F 3/033* (2013.01); *G06F 3/167* (2013.01);
(Continued)

(58) Field of Classification Search
CPC ........ G06T 11/00; G16H 50/50; G16H 10/60; G16H 40/20; G16H 30/20; G16H 30/40;
(Continued)

(56) References Cited

U.S. PATENT DOCUMENTS 9,892,564 B1  2/2018  Cvetko et al.
11,139,071 B2  10/2021  Weaver et al.
(Continued)

*Primary Examiner* — Jimmy H Nguyen
(74) *Attorney, Agent, or Firm* — Kraguljac Law Group, LLC

(57) ABSTRACT

Systems and methods for employing virtual environmental augmentation in clinical care environments to enhance a clinician's in-the-moment knowledge, leverage past experiences of the clinician and others, and improve the quality of patient care are provided. Such virtual environmental augmentation may align with prior-established, evidence-based clinical processes and enhance the clinician's in-the-moment knowledge by extracting relevant data from one or more clinical sources and presenting a virtual representation of at least a portion of the extracted data (or a summary, exemplification, or interpretation thereof) in the clinician's field-of-view while the clinician is present in a clinical care environment and is utilizing an environmental augmentation device. Such environmental augmentation additionally may facilitate real-time documentation enabling more complete clinical records and ultimately improving the quality of patient care.

20 Claims, 8 Drawing Sheets

Related U.S. Application Data continuation of application No. 16/669,006, filed on Oct. 30, 2019, now Pat. No. 11,139,071.

(60) Provisional application No. 62/786,891, filed on Dec. 31, 2018.

(51) Int. Cl.
| | |
|---|---|
| *G06F 3/033* | (2013.01) |
| *G06F 3/16* | (2006.01) |
| *G06T 11/00* | (2006.01) |
| *G16H 30/20* | (2018.01) |
| *G16H 40/20* | (2018.01) |

(52) U.S. Cl.
CPC ............ *G06T 11/00* (2013.01); *G16H 30/20* (2018.01); *G16H 40/20* (2018.01)

(58) Field of Classification Search
CPC .......... G06F 3/033; G06F 3/167; G06F 3/013; G06F 3/012
USPC ................................................. 345/156, 7–9
See application file for complete search history.

(56) References Cited

U.S. PATENT DOCUMENTS

| | | |
|---|---|---|
| 2005/0021369 A1 | 1/2005 | Cohen et al. |
| 2010/0053069 A1 | 3/2010 | Tricoukes et al. |
| 2014/0139405 A1 | 5/2014 | Ribble et al. |
| 2015/0338915 A1 | 11/2015 | Publicover et al. |
| 2019/0254754 A1 | 8/2019 | Johnson et al. |
| 2019/0348169 A1 | 11/2019 | Gibby et al. |
| 2020/0211696 A1 | 7/2020 | Weaver et al. |

VIRTUAL AUGMENTATION OF CLINICAL CARE ENVIRONMENTS

CROSS REFERENCE TO RELATED APPLICATIONS

This application is a continuation of U.S. Non-Provisional application Ser. No. 17/482,990 entitled "VIRTUAL AUGMENTATION OF CLINICAL CARE ENVIRONMENTS", and filed on Sep. 23, 2021 which is a continuation of U.S. Non-Provisional application Ser. No. 16/669,006 entitled "VIRTUAL AUGMENTATION OF CLINICAL CARE ENVIRONMENTS", and filed on Oct. 30, 2019 which is now U.S. Pat. No. 11,139,071 which issued on Oct. 5, 2021 and claims priority to U.S. Provisional Patent Application Ser. No. 62/786,891, entitled "VIRTUAL AUGMENTATION OF CLINICAL CARE ENVIRONMENTS" and filed on Dec. 31, 2018, each of which applications are hereby incorporated by reference as if set forth in their entirety herein.

BACKGROUND

Modern clinical care involves a multitude of well-established, evidence-based workflows designed to facilitate utilization of the most relevant patient information and attainment of consistent, high-quality care outcomes. However, such modern clinical workflows often are fragmented between persons, processes and technology. Such disjointedness runs the risk of obtaining sub-optimal care outcomes if, for instances, process steps are forgotten or overlooked and/or if relevant patient information is unknown or cannot easily be located when needed. Although electronic health records have become established as the neural network of clinical care, integration and dissemination of the right information, at the right time and in an intelligible manner so as to ensure the highest quality patient care outcomes remains somewhat elusive. Clinicians utilizing electronic health records must click, scroll and navigate through the technology to locate and discern appropriate information at the time it is needed. Due to missed information or information a clinician may not even know to search for, clinicians are at risk of not having a complete picture of all relevant information during moments of decision making. This, in turn, increases the risk of attaining sub-optimal clinical care outcomes.

A number of methods and systems to alleviate these concerns and provide the most relevant information at the time it is needed have been developed. For instance, when walking through an emergency room, a clinician (or other healthcare team member) may audibly and visually experience a plethora of information from a myriad of beeps and buzzes, to visual displays showing guesses on a user's intent (e.g., via presentation of "related results," and the like). However, in many such situations, all of the responsibility still falls on the clinician to know the information they want to view and to conduct a search to locate and consume such information. While all of these methods of communication are well intended, whether they show up in a toolbar of a computing device screen display, on a wearable device (such as a smart watch), or amongst a noisy environment, none of them is capable of contextualizing the overall complexity of clinical care into reality.

Recent advances in computing and display technologies have facilitated the development of systems for "virtual reality" and "augmented reality" experiences-experiences in which digitally reproduced images or portions thereof are presented to a user in such a manner that they seem to be, or may be perceived as, really existing in the user's surroundings. A virtual reality scenario typically involves presentation of digital or virtual image information void of transparency to other actual real-world visual input. By way of contrast, an augmented reality scenario typically involves presentation of digital or virtual image information as an augmentation to real-world visual input surrounding the user. For example, an augmented reality scene may allow a user of augmented reality technology to see one or more virtual objects super-imposed on or amidst real world objects.

SUMMARY

The present technology generally relates to devices, systems, and methods for employing virtual environmental augmentation in clinical care environments to enhance a clinician's in-the-moment knowledge, leverage past experiences of the clinician and others, and improve the quality of patient care. In aspects, environmental augmentation may align with prior-established clinical processes and enhance the clinician's in-the-moment knowledge by extracting relevant data from one or more clinical sources and presenting a virtual representation of at least a portion of the extracted data (or a summary, exemplification, or interpretation thereof) in the clinician's field-of-view while the clinician is present in a clinical care environment and is utilizing an environmental augmentation device. In aspects, such virtual environmental augmentation additionally may facilitate real-time documentation enabling more complete clinical records and ultimately improving the quality of patient care.

In brief, and at a high level, the present disclosure describes technology that may seamlessly integrate a clinical care environment and evidence-based clinical processes with data relevant to a patient's care through utilization of virtual environmental augmentation devices. Such devices may include, by way of example only, Magic Leap One®, Occulus Rift®, GoogleGlass®, or Microsoft HoloLens®. Image data pertaining to a field-of-view of a user (e.g., clinician) of a virtual environmental augmentation device may be received. Data aligning with up-to-date, evidence-based clinical processes may be extracted from one or more data sources. Such data may include, by way of example only, data extracted from a patient's electronic health records, population health data, workforce/operations data (e.g., floor plans, room layouts, healthcare team member assignments, etc. for a clinical facility or other clinical care environment), and device data (e.g., assigned medical equipment locations data, medical device readings, and the like). A virtual representation of at least a portion of the extracted data (or a summary, exemplification, or interpretation thereof) may be presented (in real-time or near-real-time) in the clinician's field-of-view, for instance, overlaying real-world objects present in the clinician's field-of-view as evidenced by the image data, while the clinician is present in the clinical care environment and is utilizing the environmental augmentation device.

In this way, many of the problems associated with a lack of contextualization of the overall complexity of clinical care into reality are alleviated by embodiments of the present disclosure. Clinicians (and other healthcare team members) may be provided the information most relevant to the care of patients at the time such information is needed and in the context of appropriate, evidence-based workflows. Thus, clinicians may more efficiently accomplish their daily tasks while insuring optimal care outcomes for their patients.

One aspect of the present technology that may accomplish these objectives is a system for virtually augmenting a clinical care environment. The system may include an image capture device that captures one or more images corresponding to a field-of-view of a user of an environmental augmentation device, a processor in communication with the image capture device and an electronic healthcare information system, and one or more computer-readable media storing computer-readable instructions. When the computer-readable instructions are executed by the processor, the processor is caused to: receive data relevant to a location of the user of the environmental augmentation device; receive the one or more images captured by the image capture device, the one or more images corresponding to the field-of-view of the user; receive data relevant to a patient associated with the location of the user of the environmental augmentation device; and present a virtual representation of at least a portion of the data relevant to the patient as an augmentation to the field-of-view of the user.

Another aspect of the present technology that may accomplish the above objectives is a system for virtually augmenting a clinical care environment. The system includes an image capture device that captures one or more images corresponding to a field-of-view of a user of an environmental augmentation device, a processor in communication with the image capture device and an electronic healthcare information system, and one or more computer-readable media storing computer-readable instructions. When the computer-readable instructions are executed by the processor, the processor is caused to: receive data relevant to a location of the user of the environmental augmentation device within the clinical care environment; receive the one or more images captured by the image capture device, the one or more images corresponding to the field-of-view of the user; receive data relevant to a patient associated with the location of the user of the environmental augmentation device; responsive to the data relevant to the patient, determine at least one clinical workflow relevant to care of the patient; determine a portion of the data relevant to the patient to present as an augmentation to the field-of-view of the user based, at least in part, on the at least one clinical workflow; and present a virtual representation of the portion of the data relevant to the patient as the augmentation to the field-of-view of the user.

Yet another aspect of the present technology that may accomplish the above objectives is a method for virtually augmenting a clinical care environment. The method may include: (1) receiving data relevant to a location of a user of an environmental augmentation device within the clinical care environment; (2) receiving one or more images from an image capture device, the one or more images corresponding to a field-of-view of the user; (3) receiving data relevant to a patient associated with the location of the user of the environmental augmentation device; (4) responsive to the data relevant to the patient, determining at least one clinical workflow relevant to care of the patient; (5) determining a portion of the data relevant to the patient to present as an augmentation to the field-of-view of the user based, at least in part, on the at least one clinical workflow; and (6) presenting a virtual representation of the portion of the data relevant to the patient as the augmentation to the field-of-view of the user.

Additional objects, advantages, and novel features of the technology are described below in the Detailed Description.

They will, in part, become apparent to those skilled in the art, or they may be learned by practice of the technology.

BRIEF DESCRIPTION OF THE DRAWINGS

The present technology is described in the Detailed Description with reference to the attached figures, wherein.

DETAILED DESCRIPTION

The subject matter of the present technology is described herein with specificity to meet statutory requirements. However, the description itself is not intended to limit the scope of this disclosure. Rather, the inventors have contemplated that the claimed subject matter also might be embodied in other ways, to include different steps or combinations of steps similar to the ones described in this document, in conjunction with other present or future technologies. Moreover, although the term "step" may be used herein to connote different elements of methods employed, the term should not be interpreted as implying any particular order among or between various steps disclosed, unless the order of individual steps is explicitly described.

Embodiments of the present technology are directed to methods, systems, devices and computer-readable media for employing virtual environmental augmentation in clinical care environments to enhance a clinician's in-the-moment knowledge, leverage past experiences of the clinician and others, and improve the quality of patient care. In aspects, environmental augmentation may align with prior-established clinical processes and enhance the clinical care experience by extracting relevant data from one or more clinical sources and presenting a virtual representation of at least a portion of the extracted data (or a summary, exemplification, or interpretation thereof) in the clinician's field-of-view while the clinician is present in a clinical care environment and is utilizing an environmental augmentation device. In aspects, such virtual environmental augmentation additionally may facilitate real-time documentation enabling more complete clinical records and ultimately improving the quality of patient care.

Figure 1:
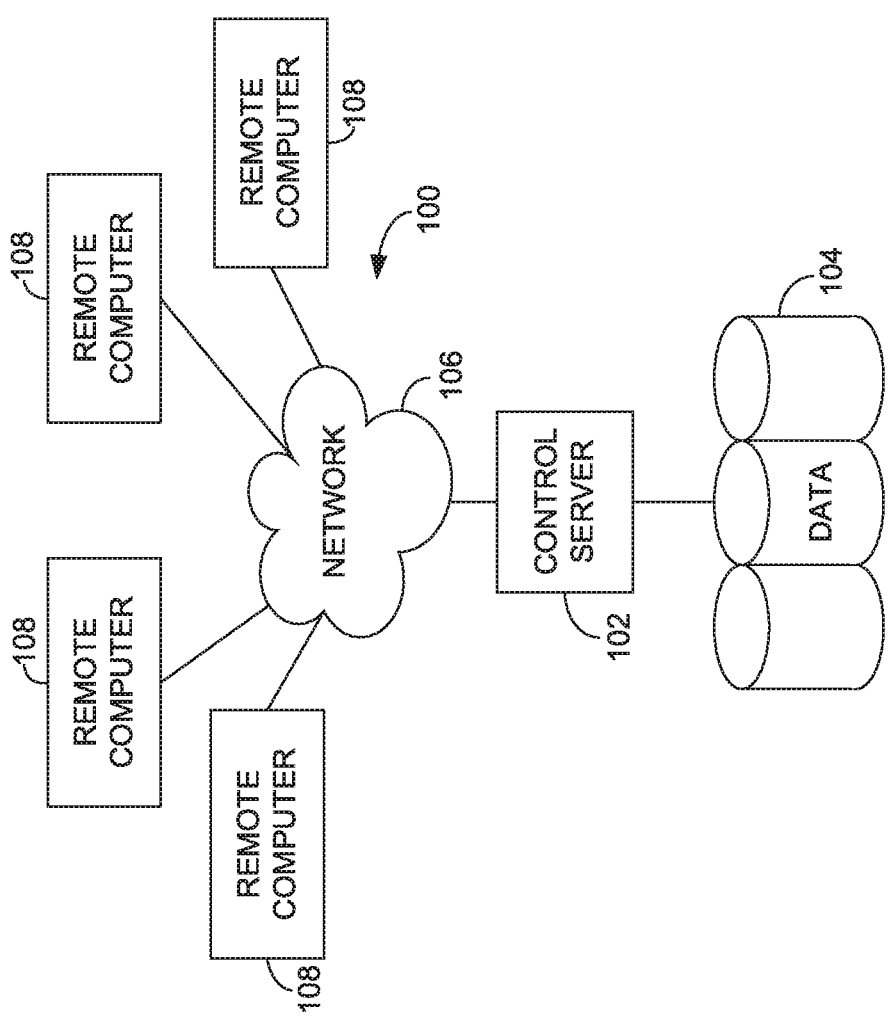
FIG. 1 is a block diagram of an exemplary computing environment suitable for use in implementing aspects of the described technology, in accordance with embodiments of the present disclosure.

With reference now to FIG. 1, an exemplary computing environment suitable for use in implementing aspects of the technology is described below. An exemplary computing environment (e.g., a medical-information computing-system environment) with which embodiments may be implemented is provided. The computing environment is merely an example of one suitable computing environment and is not intended to suggest any limitation as to the scope of use or functionality of the technology. Neither should the computing environment be interpreted as having any dependency or requirement relating to any single component or combination of components illustrated therein.

The present technology may be operational with numerous other purpose computing system environments or configurations. Examples of well-known computing systems, environments, and/or configurations that may be suitable for use with aspects of the present invention include personal computers, server computers, hand-held or laptop devices, multiprocessor systems, microprocessor-based systems, set top boxes, programmable consumer electronics, network PCs, minicomputers, mainframe computers, personal assistant devices, distributed computing environments that include any of the above-mentioned systems or devices, and the like.

The present technology may be described in the general context of computer-executable instructions, such as program modules, being executed by a computer. Exemplary program modules include routines, programs, objects, components, and data structures that perform particular tasks or implement particular abstract data types. The present technology may be practiced in distributed computing environments where tasks are performed by remote processing devices that are linked through a communications network. In a distributed computing environment, program modules may be located in association with local and/or remote computer storage media (e.g., memory storage devices).

The computing environment comprises a computing device in the form of a control server 102. Exemplary components of the control server comprise a processing unit, internal system memory, and a suitable system bus for coupling various system components, including data stores, with the control server. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes, or has access to, a variety of non-transitory computer-readable media. Computer-readable media can be any available media that may be accessed by the control server 102, and includes volatile and nonvolatile media, as well as, removable and non-removable media. By way of example, and not limitation, computer-readable media may comprise computer storage media and communication media. Computer storage media includes volatile, nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above also should be included within the scope of computer-readable media.

The control server 102 may operate in a computer network using logical connections to one or more remote computers 108. The remote computers 108 may be located at a variety of locations including operating systems, device drivers and medical information workflows. The remote computers also may be physically located in traditional and nontraditional medical care environments so that the entire healthcare community may be capable of integration on the network. The remote computers might be personal computers, servers, routers, network PCs, peer devices, other common network nodes, or the like and might comprise some or all of the elements described above in relation to the control server 102. The remote computers can be personal digital assistants or other like devices.

The computer network 106 may comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof may be stored in association with the control server 102, the data store 104, or any of the remote computers 108. For example, various application programs may reside on the memory associated with any one or more of the remote computers 108. It will be understood and appreciated by those of ordinary skill in the art that the network connections shown are exemplary and other means of establishing a communications link between the computers (e.g., the control server 102 and the remote computers 108) may be utilized.

In operation, an organization may enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information also may be sent directly from a remote healthcare device to the control server 102. In addition to a monitor, the control server 102 and/or the remote computers 108 may comprise other peripheral output devices, such as speakers and a printer.

Although many other internal components of the control server 102 and the remote computers 108 are not shown, such components and their interconnection are well known.

Accordingly, additional details concerning the internal construction of the control server 102 and the remote computers 108 are not further disclosed herein.

Image data pertaining to a field-of-view of a user (e.g., clinician) of a virtual environmental augmentation device may be received. Data aligning with up-to-date, evidence-based clinical processes may be extracted from one or more data sources. Such data may include, by way of example only, data extracted from a patient's electronic health records, population health data, workforce/operations data (e.g., floor plans, room layouts, healthcare team member assignments, etc. for a clinical facility or other clinical care environment), and device data (e.g., assigned medical equipment locations data, medical device readings, and the like). A virtual representation of at least a portion of the extracted data (or a summary, exemplification, or interpretation thereof) may be presented (in real-time or near-real-time) in the clinician's field-of-view, for instance, overlaying real-world objects present in the clinician's field-of-view as evidenced by the image data, while the clinician is present in the clinical care environment and is utilizing the environmental augmentation device.

Figure 2:
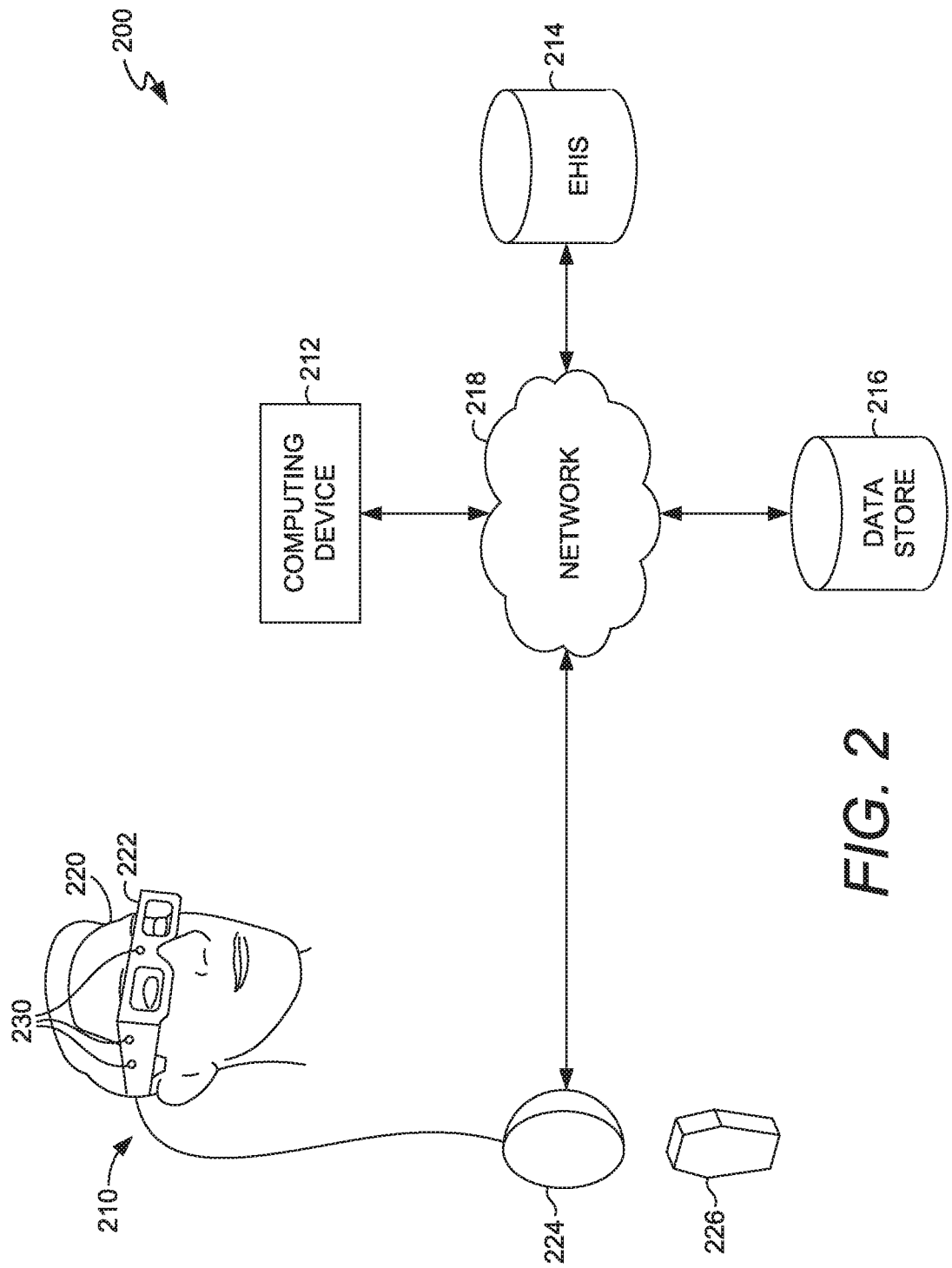
FIG. 2 is a block diagram of an exemplary system for virtually augmenting a clinical care environment, in accordance with embodiments of the present disclosure.

Turning now to FIG. 2, illustrated is a block diagram of an exemplary system 200 for virtually augmenting a clinical care environment in real-time or near-real-time. In the illustrated aspect, the system comprises an environmental augmentation device 210, one or more user computing devices/servers 212, an Electronic Health Information System (EHIS) 214, and a data store 216, all in communication with one another through a network 218. The network 218 may be any type of communication scheme that allows devices to exchange data. For example, the network 218 may include fiber optic, wired and/or wireless communication capability in any of a plurality of protocols, such as TCP/IP, Ethernet, WAP, IEEE 802.11, or any other protocols. Implementations are contemplated in which the system 200 may be accessible through a shared public infrastructure (e.g., the Internet), an extranet, an intranet, a virtual private network (VPN), a local area network (LAN), a wide area network (WAN), a peer-to-peer (P2P) network, a wireless communications network, a telephone network, a facsimile network, a cloud network, or any combination thereof. Such networks are commonplace in today's computing environments and, accordingly, are not further described herein. Although many of the components illustrated in FIG. 2 are described as individual components or functional entities, in some cases, they may be implemented as discrete or distributed components, or in conjunction with other components, having any suitable location or combination.

The virtual environmental augmentation device 210 may be a device that is configured to present digital or virtual image information as an augmentation to real-world visual input surrounding a user. For example, an augmented reality scene may allow a user of the virtual environmental augmentation device 210 to view one or more virtual objects super-imposed on or amidst real world objects in the user's field-of-view. Various virtual environmental augmentation devices 210 may be utilized in accordance with embodiments of the present disclosure including, without limitation, Magic Leap One®, Occulus Rift®, GoogleGlass®, or Microsoft Hololens®. Generally, a virtual environmental augmentation device 210 usable in accordance with embodiments of the present disclosure may include some form of physical display, such as glasses, goggles, or a helmet-mounted display, that projects or superimposes computer-generated images and/or text onto the user's view of the real world. In the exemplary embodiment illustrated in FIG. 2, the environmental augmentation device 210 includes glasses 222 as a head-mounted display.

In addition to glasses 222, the environmental augmentation device 210 illustrated in FIG. 2 includes a computing unit 224, a controller 226, an image capture device 228 and a plurality of sensors 230. The computing unit 224 may include one or more processors, for instance, an integrated Graphics Processing Unit (GPU) and/or an integrated Central Processing Unit (CPU). In embodiments, the computing unit 224 may include a battery, such as a rechargeable battery, such that the computing unit 224 does not require a wired connection to a power source but rather may be communicatively coupled to one or more other devices (e.g., the computing device 212, the Electronic Health Information System (EHIS) 214, and/or the data store 216) via Bluetooth® or other wireless connection. In various embodiments, the computing unit 224 may include a number of components, examples of which are illustrated with reference to FIG. 3 (more fully described below).

The controller 226 may be a handheld component configured for registering non-verbal user commands. Such commands may be expressed, by way of example only, by clicking of a selection button included in association with the controller 226 while the controller (or an indicator thereof) is in proximity to virtual information with which the user desires to interact, or waving or otherwise gesturing the controller 226 in a direction of virtual information with which the user desires to interact. In some embodiments, the controller 226 may be a headset comprising the glasses 222. Commands may be expressed, by way of example only, by eye gaze and head positioning, as detected by the controller 226 and/or glasses 222 or a component thereof (e.g., a sensor), while the controller (or an indicator thereof) is in proximity to virtual information with which the user desires to interact.

The image capture device 228 may be configured to capture one or more images corresponding to a field-of-view of a user of the environmental augmentation device, e.g., the user 220. In embodiments, the image capture device 228 may be a camera. In embodiments, the camera may include three-dimensional and/or video recording capability.

The one or more sensors 230 may include any sensors known to those having ordinary skill in the art configured for sensing information in the environment surrounding the user 220 of the environmental augmentation device 210 and/or outputting information into the surrounding environment. Such sensors 230 may include, by way of example only, a location sensor (e.g., a global positioning system (GPS) sensor and/or an Real-Time Location System (RTLS) sensor), a listening component (e.g., a microphone), an eye-movement or eye-tracking sensor, and/or a speaker. In embodiments, the one or more sensors 230 may facilitate documentation of sensed information in association with electronic health records of patients or otherwise in association with an Electronic Health Information System (EHIS), e.g., the EHIS 214 of FIG. 2. Additionally, interactions by the controller 226 and/or glasses 222 may be logged in the electronic health records of patients.

Figure 3:
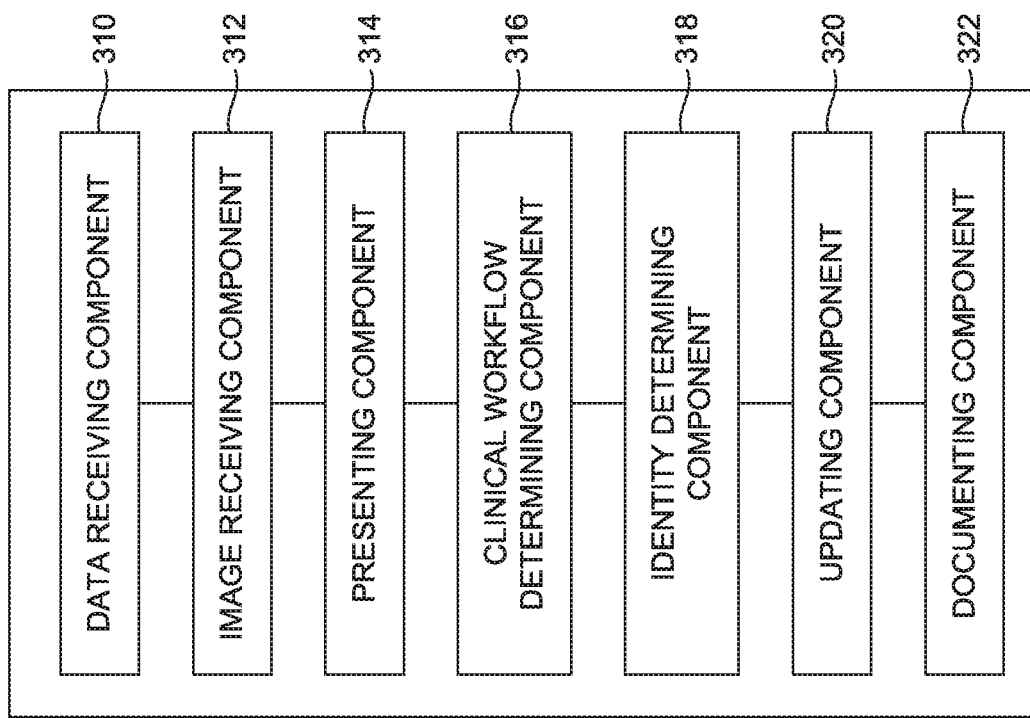
FIG. 3 is a block diagram of an exemplary computing unit of an environmental augmentation device, in accordance with embodiments of the present disclosure.

Turning now to FIG. 3, illustrated are various components that may be included in the computing unit 224 of the environmental augmentation device 210 of FIG. 2. As illustrated, the components include a data receiving/extracting component 310, an image receiving component 312, a presenting component 314, a clinical workflow determining component 316, an identity determining component 318, an updating component 320 and a documenting component 322.

The data receiving/extracting component 310 may be configured for receiving data relevant to a location of a user of an environmental augmentation device (e.g., the user 220 of the environmental augmentation device 210 of FIG. 2). Such data may be received, for instance, from a data store (e.g., the data store 216 of FIG. 2) that includes a mapping of the clinical care environment of the user in cooperation with real-time location services that may be capable of identifying a current location of the user and matching the user's current location to a location on the mapping. In some cases, the mapping of the clinical care environment may be performed by the environmental augmentation device. In some cases, the environmental augmentation device may include a sensor (such as a GPS sensor or RTLS sensor) for determining a current location of the user. In some cases, the user may have a separate device that includes a sensor (e.g., a GPS sensor or a RTLS sensor) for facilitating determination of his or her current location.

In embodiments, the data receiving/extracting component 310 further may be configured for receiving data relevant to a patient associated with a location of a user of an environmental augmentation device (e.g., a location of the user 220 of the environmental augmentation device 210 of FIG. 2). In some cases, the data relevant to the patient may include, by way of example only, data related to diagnoses, conditions, medications, family history, previous clinical care visits, and the like related to the patient, as well as, for instance, a reason that the patient is currently located in the clinical care environment. In some cases, the location of the user may include an area surrounding the user and may not be limited to the user's exact location. For instance, a determined user location may be in a hallway outside of a door into a hospital room and the location of the user, for instance, for purposes of determining a patient associated with the location of the user (such determination being made by the identity determining component 318), may be viewed broadly enough to include the hospital room and thus the patient occupying the room.

In embodiments, the data receiving/extracting component 310 further may be configured for determining at least a portion of data relevant to a patient to present as an augmentation to the field-of-view of a user of an environmental augmentation device based, at least in part, on at least one clinical workflow (e.g., a clinical workflow determined to be relevant to the patient by the clinical workflow determining component 316, more fully described below).

The image receiving component 312 may be configured for receiving one or more images captured by an image capture device. In embodiments, the received images may correspond to a field-of-view of the user of the environmental augmentation device. In some cases, the images may be captured by an image capture device associated with an environmental augmentation device (e.g., the image capture device 216 of the environmental augmentation device 210 of FIG. 2). In some cases, the image capture device may be separate from the environmental augmentation device and images captured thereby may be transmitted to the environmental augmentation device (and received by the image receiving component 312) as appropriate. In embodiments, the image capture device may be a camera. In embodiments, the camera may include three-dimensional and/or video recording capability.

The presenting component 314 may be configured for presenting a virtual representation of at least a portion of data received as relevant to a patient (or a summary, exemplification, or interpretation thereof) as a virtual augmentation to the field-of-view of the user (e.g., the user 220 of FIG. 2). In some cases, the presenting component 214 further may be configured to present a virtual representation of information other than the portion of the patient data. By way of a non-limiting example, such information may include steps of a clinical workflow relevant to the patient and in which the user may be engaged, a current status of the patient and/or the user within a relevant clinical workflow, and/or information regarding the user's progress with regard to his or her daily workflow.

The clinical workflow determining component 316 may be configured for, responsive to data received as relevant to a patient, determining at least one clinical workflow relevant to care of the patient. Such determination may be made, by way of example only and not limitation, based upon the patient's reason for being in the clinical care environment, a diagnosis of the patient, a condition of the patient, a symptom of the patient, family history of the patient, information pertaining to previous clinical care visits of the patient, population health data pertaining to the patient, and the like. Relevant clinical workflows further may be determined as corresponding to up-do-date, evidence-based clinical processes known to those having ordinary skill in the art.

The identity determining component 318 may be configured for determining an identity of a patient associated with a location of a user of an environmental augmentation device. In some cases, the location of the user of an environmental augmentation device (e.g., the user 220 of the environmental augmentation device 210 of FIG. 2) may include an area surrounding the user and not be limited to the user's exact location. For instance, the user location may be in a hallway outside of a door into a hospital room and the location of the user, for instance, for purposes of determining a patient associated with the location of the user, may be expanded to include the hospital room and thus the patient occupying the room. The identity determining component 318 may be configured for determining an identity of the patient by utilizing the location of the user and comparing the location to information (stored, e.g., in association with the data store 216, the EHIS 214 or the computing device 212 of FIG. 2) pertaining to the patient's current location in the clinical care environment and/or patient assignment information for the broader clinical care environment.

Figure 8:
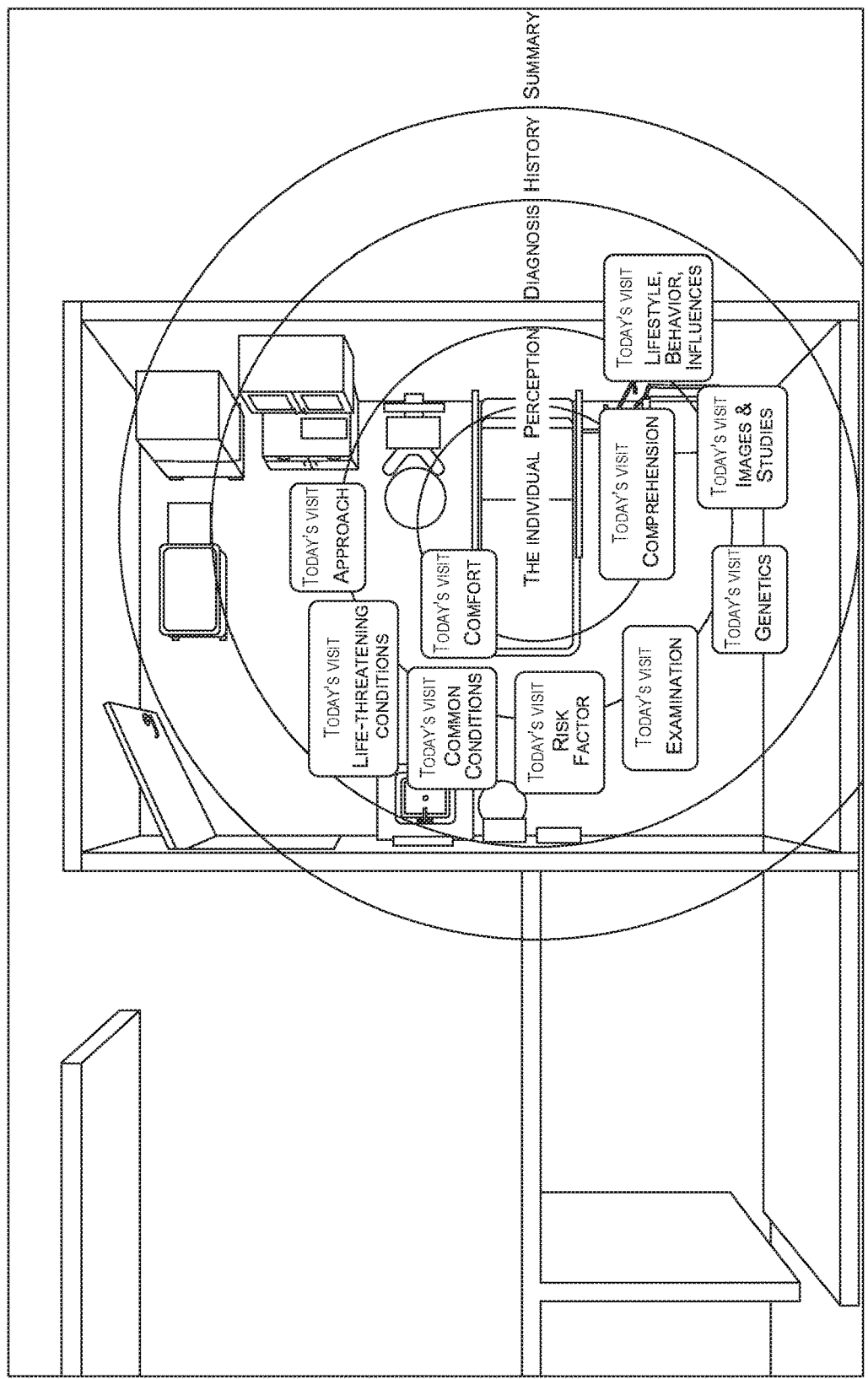
FIG. 8 is a schematic diagram illustrating an exemplary model-based layout for displaying information in an augmented field-of-view, in accordance with embodiments of the present disclosure.

The updating component 320 may be configured for automatically updating the location of a user of an environmental augmentation device as the user's location changes, for instance, as the user moves throughout the clinical care environment. Such changes may be simply in the direction of the user's stance within a particular location of the clinical care environment (e.g., the direction the user is facing within a room) such that the field-of-view of the user changes or such change may be farther reaching, for instance, a change in the user's location such that a patient determined to be associated with the user's location changes as well. Based upon the field-of-view of the user, different information may be presented to the user. In this way, users of the environmental augmentation device may come to rely on being able to find certain information (e.g., family history information) in a certain location of their field-of-view as it pertains to their directional stance within a particular location (e.g., within a hospital room). In embodiments, the standard locations where items of information may be found may be associated with a model clinician's are familiar with such as, by way of example only, the Bohr model of an atom. By way of example only, FIG. 8 shows a schematic diagram illustrating an exemplary model-based layout for displaying information in an augmented field-of-view, in accordance with embodiments of the present disclosure.

The documenting component 322 may be configured for documenting at least a portion of actions taken by the user and/or the patient (e.g., actions sensed by an image capture device) and/or received verbal commands (e.g., verbal commands of the user sensed by a listening component, e.g., a microphone) in association with a patient in an electronic healthcare information system (e.g., the EHIS 214 of FIG. 2). In this way, documentation of patient interactions with healthcare team members may be more completed more efficiently, ultimately leading to more thorough records. In embodiments, the documenting component 322 further may be configured to document actions completed by the user via a controller (e.g., the controller 226 of FIG. 2) and or actions completed or undertaken via a clinician's eye gaze (for instance, utilizing an eye-gaze or eye-tracking sensor).

Figure 4:
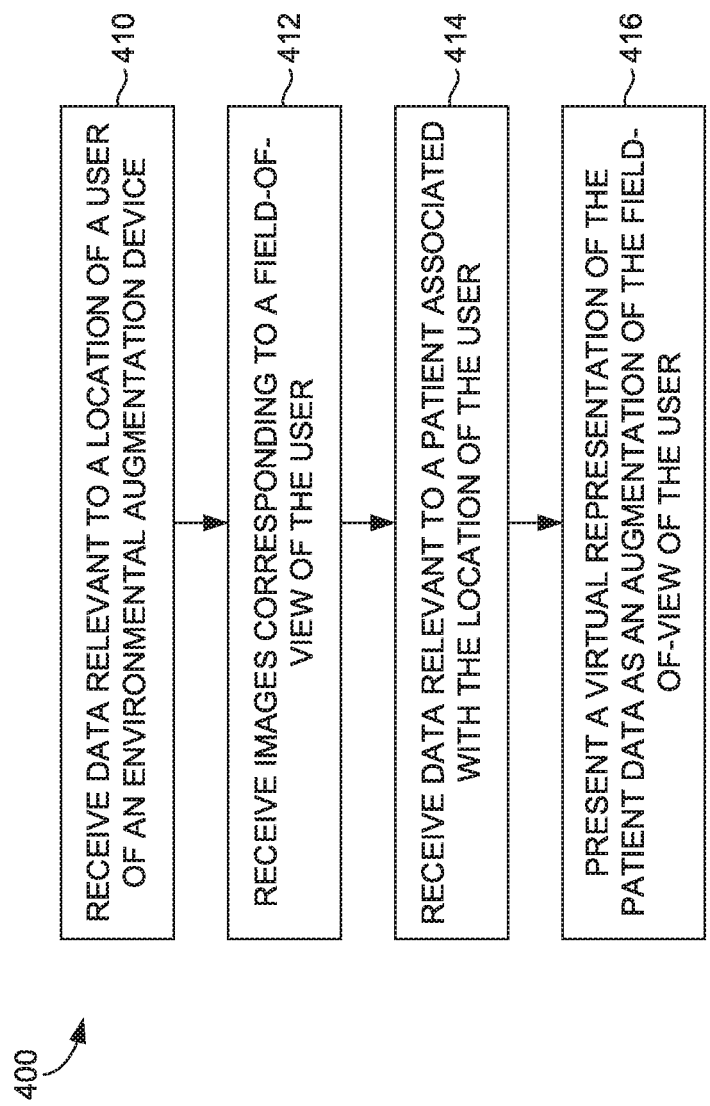
FIG. 4 is a block diagram of an exemplary method for virtually augmenting a clinical care environment, in accordance with embodiments of the present disclosure.

With reference now to FIG. 4, illustrated is a flow diagram of an exemplary method 400 for virtually augmenting a clinical care environment, in accordance with embodiments of the present disclosure. In some cases, a field-of-view of a user (for instance, a clinician or other healthcare provider) utilizing an environmental augmentation device (e.g., the environmental augmentation device 210 of FIG. 2) in accordance with the method 400 of FIG. 4 may be augmented to enhance the user's in-the-moment knowledge, leverage past experiences of the user and others, align patient care with evidence-based clinical workflows, provide real-time translation (e.g., closed captioning) between patient and clinician or other health provider, and improve the quality of patient care.

As indicated at block 410, data relevant to a location of the user of the environmental augmentation device (e.g., the user 220 of the environmental augmentation device 210 of FIG. 2) is received (e.g., by the data receiving/extracting component 310 of FIG. 3). Such data may be received, for instance, from a data store (e.g., the data store 216 of FIG. 2) that includes a mapping of the clinical care environment of the user in cooperation with real-time location services that may be capable of identifying a current location of the user and matching the user's current location to a location on the mapping. In some cases, the mapping of the clinical care environment may be performed by the environmental augmentation device. In some cases, the environmental augmentation device may include a sensor (such as a GPS sensor or RTLS sensor) for determining a current location of the user. In some cases, the user may have a separate device that includes a sensor (e.g., a GPS sensor or a RTLS sensor) for facilitating determination of his or her current location.

As indicated at block 412, one or more images are received (e.g., by the image receiving component 312 of FIG. 3). The images correspond to a field-of-view of the user of the environmental augmentation device (e.g., the user 220 of the environmental augmentation device 210 of FIG. 2). In some cases, the images may be captured by an image capture device associated with the environmental augmentation device (e.g., the image capture device 216 of the environmental augmentation device 210 of FIG. 2). In embodiments, the image capture device may be a camera. In embodiments, the camera may include three-dimensional and/or video recording capability.

As indicated at block 414, data relevant to a patient associated with the location of the user of the environmental augmentation device (e.g., the user 220 of the environmental augmentation device 210 of FIG. 2) may be received (e.g., by the data receiving/extracting component 310 of FIG. 3). In some cases, the data relevant to the patient may include, by way of example only, data related to diagnoses, conditions, medications, family history, previous clinical care visits, and the like related to the patient. In some cases, the location of the user may include an area surrounding the user and not be limited to the user's exact location. For instance, the user location may be in a hallway outside of a door into a hospital room and the location of the user, for instance, for purposes of determining a patient associated with the location of the user, may be expanded to include the hospital room and thus the patient occupying the room.

As indicated at block 416, a virtual representation of at least a portion of the data relevant to the patient (or a summary, exemplification, or interpretation thereof) may be presented (e.g., by the presentation component 314 of FIG. 3) as a virtual augmentation to the field-of-view of the user (e.g., the user 220 of FIG. 2). In some cases, a virtual representation of information other than the portion of the patient data may be presented as well. By way of a non-limiting example, such information may include steps of a clinical workflow relevant to the patient and in which the user may be engaged, a current status of the patient and/or the user within the relevant clinical workflow, and/or information regarding the user's progress with regard to his or her daily workflow.

Utilizing the method 400 depicted in the flow diagram of FIG. 4, a field-of-view of the user may be augmented to enhance the user's in-the-moment knowledge, leverage past experiences of the user and others, align patient care with evidence-based clinical workflows, and improve the quality of care for the patient. In embodiments, documentation of actions taken by the user and/or the patient may be facilitated as well, thus improving the quality and completeness of the clinical documentation related to the patient.

Figure 5:
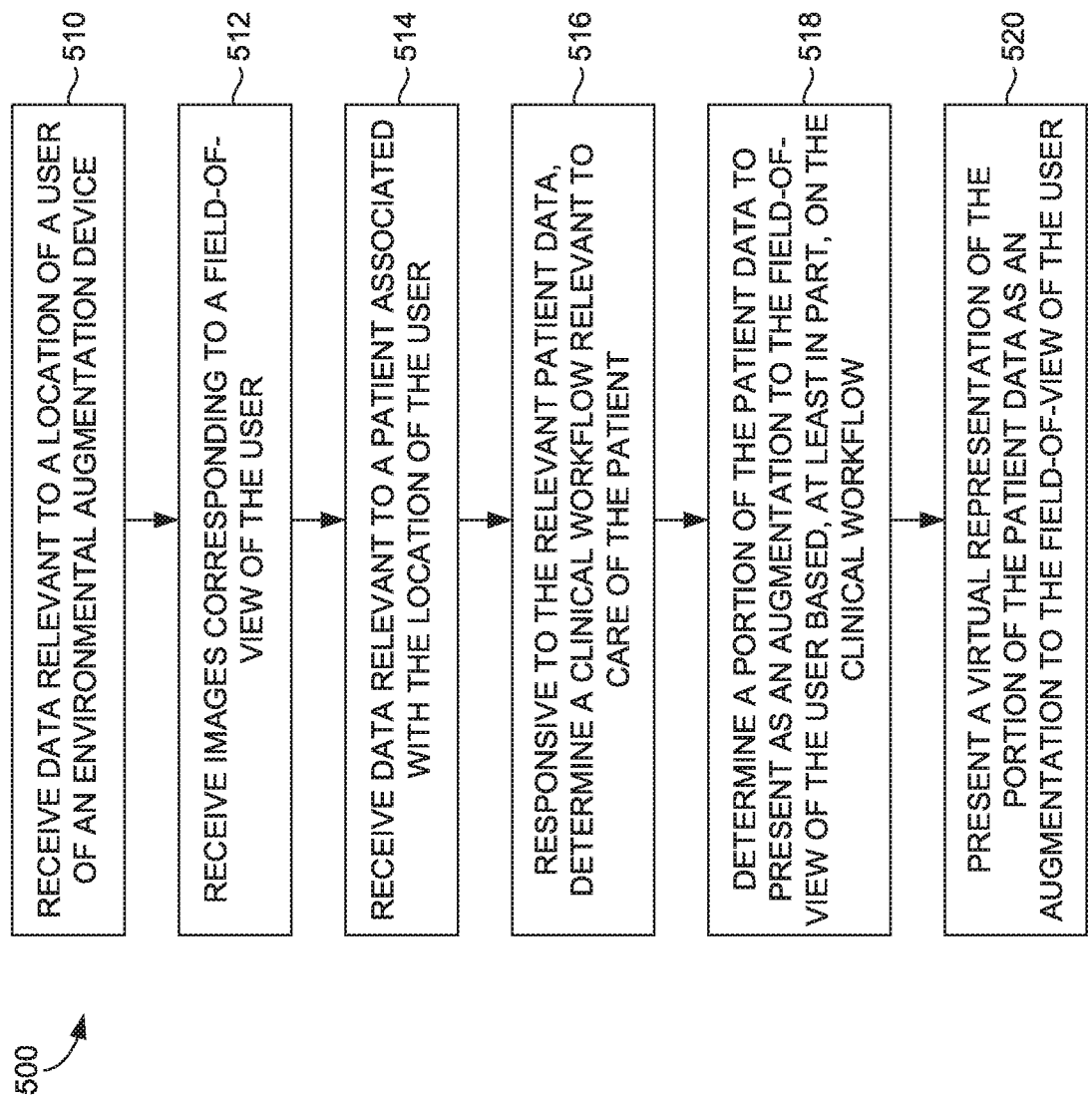
FIG. 5 is a block diagram of an exemplary method for virtually augmenting a clinical care environment, in accordance with embodiments of the present disclosure.

Turning now to FIG. 5, illustrated is a flow diagram of an exemplary method 500 for virtually augmenting a clinical care environment, in accordance with embodiments of the present disclosure. In some cases, a field-of-view of a user (for instance, a clinician or other healthcare provider) utilizing an environmental augmentation device (e.g., the environmental augmentation device 210 of FIG. 2) in accordance with the method 500 of FIG. 5 may be augmented to enhance the user's in-the-moment knowledge, leverage past experiences of the user and others, align patient care with evidence-based clinical workflows, and improve the quality of patient care.

As indicated at block 510, data relevant to a location of the user of the environmental augmentation device (e.g., the user 220 of the environmental augmentation device 210 of FIG. 2) is received (e.g., by the data receiving/extracting component 310 of FIG. 3). Such data may be received, for instance, from a data store (e.g., the data store 216 of FIG. 2) that includes a mapping of the clinical care environment of the user in cooperation with real-time location services (RTLS) that may be capable of identifying a current location of the user and matching the user's current location to a location on the mapping. In some cases, the mapping of the clinical care environment may be performed by the environmental augmentation device. In some cases, the environmental augmentation device may include a sensor (such as a GPS sensor or RTLS sensor) for determining a current location of the user. In some cases, the user may have a separate device that includes a sensor (e.g., a GPS sensor or a RTLS sensor) for facilitating determination of his or her current location.

As indicated at block 512, one or more images are received (e.g., by the image receiving component 312 of FIG. 3). The images correspond to a field-of-view of the user of the environmental augmentation device (e.g., the user 220 of the environmental augmentation device 210 of FIG. 2). In some cases, the images may be captured by an image capture device associated with the environmental augmentation device (e.g., the image capture device 216 of the environmental augmentation device 210 of FIG. 2). In embodiments, the image capture device may be a camera. In embodiments, the camera may include three-dimensional and/or video recording capability.

As indicated at block 514, data relevant to a patient associated with the location of the user of the environmental augmentation device (e.g., the user 220 of the environmental augmentation device 210 of FIG. 2) may be received (e.g., by the data receiving/extracting component 310 of FIG. 3). In some cases, the data relevant to the patient may include, by way of example only, data related to diagnoses, conditions, medications, family history, previous clinical care visits, and the like related to the patient. In some cases, the location of the user may include an area surrounding the user and not be limited to the user's exact location. For instance, the user location may be in a hallway outside of a door into a hospital room and the location of the user, for instance, for purposes of determining a patient associated with the location of the user, may be expanded to include the hospital room and thus the patient occupying the room.

As indicated at block 516, responsive to the data received as relevant to the patient, at least one clinical workflow relevant to care of the patient may be determined (e.g., by the clinical workflow determining component 316 of FIG. 3). Such determination may be made, by way of example only and not limitation, based upon the patient's reason for being in the clinical care environment, a diagnosis of the patient, a condition of the patient, a symptom of the patient, family history of the patient, information pertaining to previous clinical care visits of the patient, population health data pertaining to the patient, and the like.

As indicated at block 518, based, at least in part, upon the at least one determined clinical workflow, a portion of the data relevant to the patient may be determined (e.g., by the data receiving/extracting component 310 of FIG. 3) to present as an augmentation to the field-of-view of the user. As indicated at block 520, a virtual representation of the portion of the data relevant to the patient (or a summary, exemplification, or interpretation thereof) may be presented (e.g., by the presentation component 314 of FIG. 3) as a virtual augmentation to the field-of-view of the user (e.g., the user 220 of FIG. 2). In some cases, a virtual representation of information other than the portion of the patient data may be presented as well. By way of a non-limiting example, such information may include steps of a clinical workflow relevant to the patient and in which the user may be engaged, a current status of the patient and/or the user within the relevant clinical workflow, and/or information regarding the user's progress with regard to his or her daily workflow.

Utilizing the method 500 depicted in the flow diagram of FIG. 5, a field-of-view of the user may be augmented to enhance the user's in-the-moment knowledge, leverage past experiences of the user and others, align patient care with evidence-based clinical workflows, and improve the quality of care for the patient. In embodiments, documentation of actions taken by the user and/or the patient may be facilitated as well, thus improving the quality and completeness of the clinical documentation related to the patient.

Figure 6:
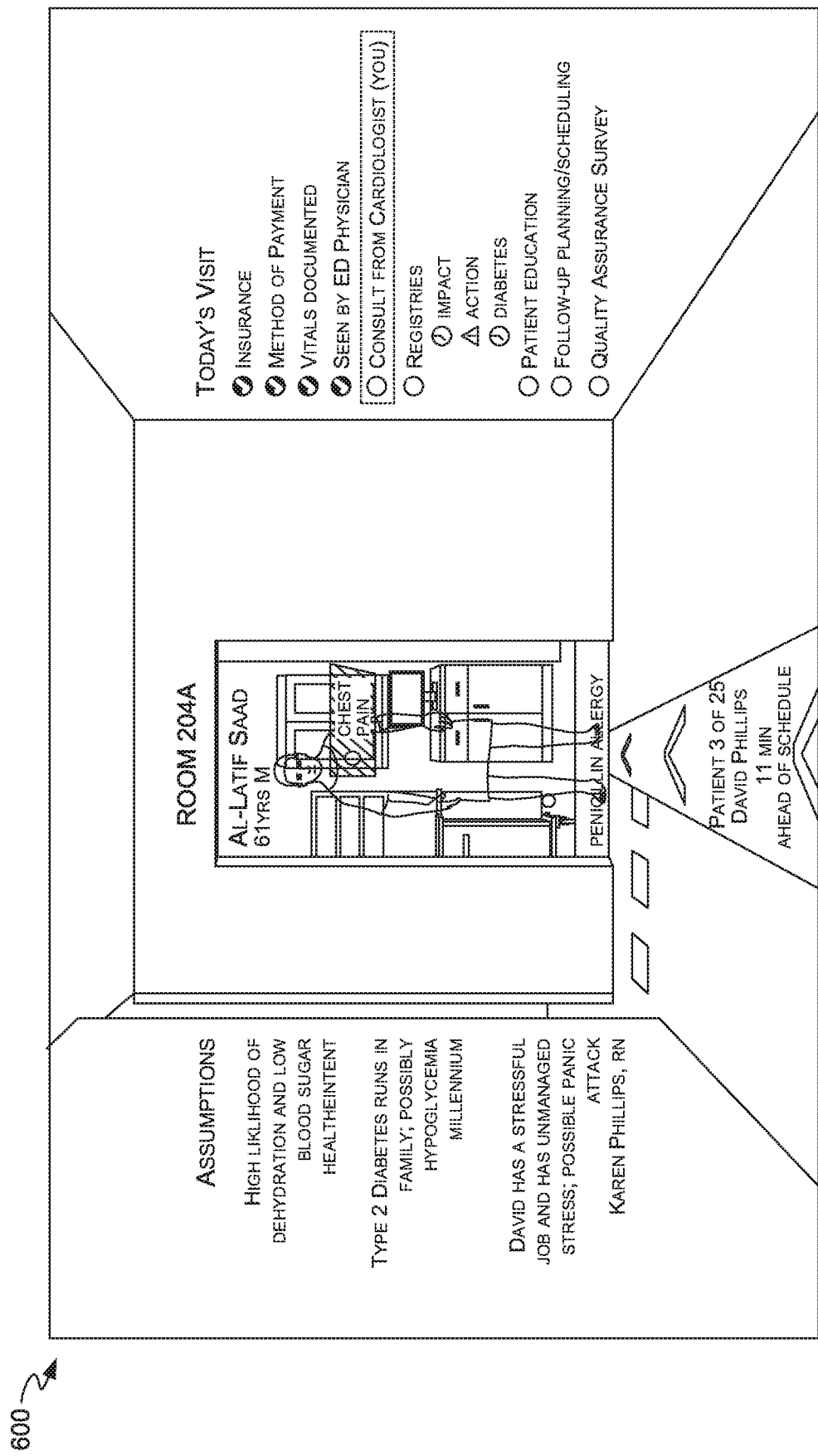
FIG. 6 is an exemplary view of a clinician's augmented field-of-view upon approach to a hospital room occupied by a patient by the name of Al-Latif Saad, in accordance with embodiments of the present disclosure.

Turning now to FIG. 6, illustrated is an exemplary view 600 of a clinician's augmented field-of-view upon approach to a hospital room occupied by a patient by the name of Al-Latif Saad, in accordance with embodiments of the present disclosure. As can be seen, the patient Al-Latif Saad has been identified as a patient associated with the location of the user of an environmental augmentation device. As the user approaches the room, the identity of the patient is presented as well as additional information deemed relevant to the clinician's visit with the patient. Assumptions regarding symptoms and the like based upon previous visits are listed to the left of the doorway. The steps comprising a workflow for the days visit is shown to the right of the doorway. Checked are those steps already completed and highlighted is the step in which the user is currently engaged. The steps that are neither highlighted nor checked have yet to be completed for the day's visit. The floor indicates where the clinician stands in his or her daily workflow (he or she is 11 minutes ahead of schedule, he is on patient number two and patient number three of twenty-five, by the name of David Phillips, is his or her next appointment). Highlighted on the virtual image of the patient Is his primary symptom or reason for being in the clinical environment on the present day.

Of particular note is the notation that the patient has a Penicillin Allergy near the base of the doorway. This information is highlighted in red as it is deemed of particular importance. In embodiments, in order for this information to be removed from the field-of-view of the clinician (that is, the user of the environmental augmentation device), the clinician must physically interact with the information (e.g., step over it or kick through it) indicating that the information has been viewed and understood by the clinician.

Figure 7:
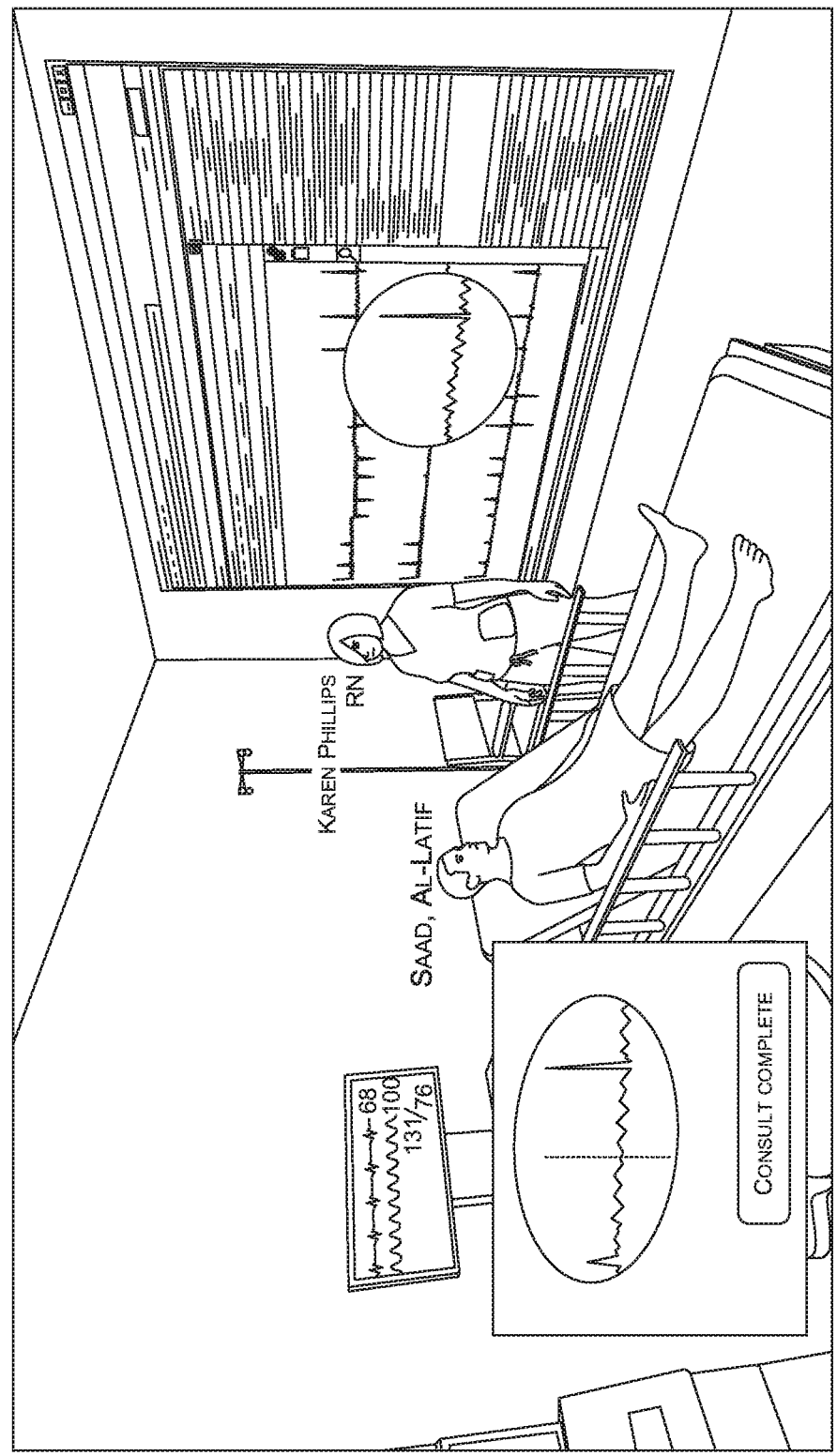
FIG. 7 is an exemplary view of a clinician's augmented field-of-view upon entering the hospital room occupied by the patient Al-Latif Saad, in accordance with embodiments of the present disclosure.

Turning now to FIG. 7 an exemplary view 700 of the clinician's augmented field-of-view upon entering the hospital room occupied by the patient Al-Latif Saad is shown, in accordance with embodiments of the present disclosure. As illustrated, the patient name and the name of another team member present in the room have been utilized to augment the clinician's field-of-view. Also augmenting the field-of-view is information derived from the patient's chart (as shown on the wall on the right-hand side of the view). In embodiments, this information may be static and stored in association with the patient's electronic health records in an EHIS. In embodiments, this information (or any information desired) may be live-streamed into the user's field-of-view.

In FIG. 8, an exemplary model-based layout 800 for displaying information in an augmented field-of-view is provided, in accordance with embodiments of the present disclosure. In this layout 800, an aerial view provides data structured around the patient in a series of rings. Each ring reflects the data or information most appropriate to present to the clinician. For instance, the outer most ring may have information shown at the door of the room (e.g., the view of FIG. 7). In contrast, data that is critical to care may be shown directly next to the patient.

From the foregoing, it will be seen that the disclosed technology is one well adapted to attain all the ends and objects described, together with other advantages which are obvious and inherent to the structure. It will be understood that certain features and sub-combinations are of utility and may be employed without reference to other features and sub-combinations. This is contemplated by and is within the scope of the claims. Since many possible embodiments may be made of the present technology without departing from the scope, it is to be understood that all matter described or shown in the accompanying drawings is to be interpreted as illustrative and not in a limiting sense.

What is claimed is:

1. An environmental augmentation device, comprising:
a computing unit including a processor;
a location sensor;

a display;
wherein the environmental augmentation device is configured to:
  access appointments of patients that a user is to visit on a schedule, wherein each appointment corresponds to a patient;
  sense that the environmental augmentation device is at a current location within an environment using the location sensor;
  detect that the current location corresponds to a location of a patient; and
  in response to the detection, generate in the display an indication of progress of the user through the appointments of patients at the current location.

2. The environmental augmentation device of claim 1, wherein the display superimposes the generated indication of progress onto a view of the user of the environment.

3. The environmental augmentation device of claim 1, wherein the sensing that the environmental augmentation device is at the current location within the environment using the location sensor includes determining the current location based on sensing a global positioning system signal or a real-time location service signal by the location sensor.

4. The environmental augmentation device of claim 1, wherein the location of the patient is a room assigned to the patient.

5. The environmental augmentation device of claim 1, wherein generating in the display the indication of progress of the user further includes
  generating in the display a statement of an amount of time by which the user is ahead of or behind the schedule for a next patient.

6. The environmental augmentation device of claim 1, wherein generating in the display the indication of progress of the user further includes
  generating in the display a name of a next patient and a number of the next patient with respect to a total number of appointments of patients in the schedule.

7. The environmental augmentation device of claim 1, wherein the environmental augmentation device is further configured to:
  access from an electronic health information service an electronic health record of the patient; and
  generate in the display additional information from the electronic health record, wherein the additional information is relevant to a visit of the user to the patient.

8. The environmental augmentation device of claim 1, wherein at least the location sensor and display are configured to be on the person of the user.

9. The environmental augmentation device of claim 1, wherein the environment is a clinical care environment, the user is a clinician, and the daily workflow includes a schedule of visits of the clinician with patients of the clinician.

10. A computer-implemented method, comprising:
  accessing appointments with patients within a clinical care environment that a clinician is to visit on a schedule, wherein each appointment corresponds to a patient;
  sensing that an environmental augmentation device is at a current location within the clinical care environment using a location sensor;
  detecting that the current location corresponds to a location of a patient; and
  in response to the detection, generating in a display an indication of progress of the clinician through the appointments with patients at the current location, wherein the display superimposes the generated indication of progress onto a view of the clinician of the clinical care environment.

11. The method of claim 10, wherein the sensing that the environmental augmentation device is at the current location within the clinical care environment using the location sensor further comprises determining the current location based on sensing a global positioning system signal or a real-time location service signal by the location sensor.

12. The method of claim 10, wherein the detecting that the current location corresponds to the location of the patient included in the workflow further comprises determining that the current location is within a ring around the patient.

13. The method of claim 10, wherein the generating in the display the indication of progress of the clinician further comprises:
  determining an extent to which the clinician is ahead of or behind the schedule;
  determining a name of a next patient in the appointments with patients; and
  generating in the display the name of the next patient and a statement of amount of time by which the clinician is ahead of or behind the schedule.

14. The method of claim 10, further comprising:
  accessing from an electronic health information service an electronic health record of the patient; and
  generating in the display additional information from the electronic health record, wherein the additional information is relevant to a visit of the clinician to the patient.

15. One or more non-transitory computer-readable media that include stored thereon computer-executable instructions that when executed by at least a processor of a computer cause the computer to:
  access appointments with patients within a clinical care environment that a clinician is to visit on a schedule, wherein individual appointment corresponds to individual patient;
  sense that the clinician is at a current location within the clinical care environment using a location sensor borne by the clinician;
  detect that the current location corresponds to a location of a patient with whom the clinician has an appointment; and
  in response to the detection, generate in a display an indication of progress of the clinician through the appointments with patients on an arrival of the clinician at the location of the patient, wherein the display superimposes the generated indication of progress onto a view of the clinician of the clinical care environment.

16. The non-transitory computer-readable media of claim 15, wherein the instructions, when executed by at least the processor, to cause the computer to sense that the clinician is at the current location within the clinical care environment using the location sensor include instructions to determine the current location based on sensing a global positioning system signal or a real-time location service signal by the location sensor.

17. The non-transitory computer-readable media of claim 15, wherein the instructions, when executed by at least the processor, to cause the computer to detect that the current location corresponds to the location of the patient include instructions to determine that the current location satisfies a threshold with respect to the one of the locations.

18. The non-transitory computer-readable media of claim 15, wherein the instructions, when executed by at least the processor, to cause the computer to generate in the display the indication of progress of the clinician include instructions to generate in the display a name of a next patient and a statement of an extent to which the clinician is ahead of or behind the schedule.

19. The non-transitory computer-readable media of claim 15, wherein the instructions, when executed by at least the processor, further cause the computer to:
    access from an electronic health information service an electronic health record of the patient; and
    generate in the display additional information about the patient from the electronic health record.

20. The non-transitory computer-readable media of claim 15, wherein the instructions, when executed by at least the processor, to cause the computer to sense that the clinician is at current location within the clinical care environment using the location sensor include instructions to determine the current location based on sensing a real-time location service signal by the location sensor.

\* \* \* \* \*